United States Patent [19]

Yatzidis

[11] Patent Number: 4,959,175

[45] Date of Patent: Sep. 25, 1990

[54] SOLUTION FOR DIALYSES AND USE OF PEPTIDES BASED ON GLYCINE FOR PREPARING IT

[75] Inventor: Hippocrates Yatzidis, Athens, Greece

[73] Assignee: Pierre Fabre Medicament, Paris, France

[21] Appl. No.: 147,424

[22] Filed: Jan. 25, 1988

[30] Foreign Application Priority Data

Jan. 27, 1987 [GR] Greece .................................. 870129

[51] Int. Cl.$^5$ ........................ A61M 1/14; A61M 1/28; A61K 33/10; A61K 37/18
[52] U.S. Cl. .................................... 252/364; 210/646; 210/647; 252/1; 514/2; 514/970; 424/423; 604/27
[58] Field of Search ..................... 252/1, 364; 210/647, 210/646; 604/27, 29, 5

[56] References Cited

U.S. PATENT DOCUMENTS

| | | | |
|---|---|---|---|
| 4,336,881 | 6/1982 | Babb et al. | 252/1 X |
| 4,339,433 | 7/1982 | Kartinos et al. | 609/29 X |
| 4,489,535 | 12/1984 | Veltman | 252/1 X |
| 4,665,941 | 4/1987 | Suzuki | 252/1 |
| 4,761,237 | 8/1988 | Alexander et al. | 210/647 |

FOREIGN PATENT DOCUMENTS

| | | | |
|---|---|---|---|
| 86553 | 8/1983 | European Pat. Off. | 604/29 |
| 89135 | 9/1983 | European Pat. Off. | 604/29 |

OTHER PUBLICATIONS

JPO 56–2917, Patent Abstracts of Japan, Yoshida et al., Appl. #54–76734, Abstract Date 4/81.

G. Jessing et al., "Addition of Aminoacids to Peritoneal-Dialysis Fluid", The Lancet 10/12/1968.

Oreopoudos et al., "Amino Acids as an Osmotic Agent . . . ", Chem. Abstr. 93:165635u, 1980.

Klein et al., "Peptides as Substitute Osmotic Agents . . . ", Chem. Abstr. 106:23227a, 1986.

Goodship, T. H. J. et al., "Short Term Studies on the Use of Amino Acids . . . " Chem. Abstr. 108:26931c, 1987.

Primary Examiner—Richard D. Lovering
Assistant Examiner—John M. Covert
Attorney, Agent, or Firm—Pollock, Vande Sande & Priddy

[57] ABSTRACT

The present invention relates to a solution for dialyses based on bicarbonate ions and containing a peptide based on glycine, as well as to the use of this peptide for the preparation of such a solution.

7 Claims, No Drawings

SOLUTION FOR DIALYSES AND USE OF PEPTIDES BASED ON GLYCINE FOR PREPARING IT

BACKGROUND OF THE INVENTION

The present invention relates to a solution for hemodialysis or peritoneal dialysis.

Dialysis is used as a method of extrarenal purification for combating renal insufficiency: the patient's blood, overloaded with catabolites (or waste materials) is brought into contact with artificial solutions across a membrane.

Such artificial solutions have to have an electrolyte formula resembling that of normal plasma as closely as possible, and contain, for example, sodium, chloride, potassium, calcium and/or magnesium ions. Glucose is often used as an osmotic agent. By way of buffering agents, acetate and lactate ions and especially bicarbonate ions are used, the latter enabling the metabolic acidosis that frequently accompanies renal insufficiency to be combatted.

In point of fact, in the presence of lactic or acetic acid and at a pH of approximately 5.5, bicarbonate ions form complexes of the $Ca(HCO_3)_2$ or $Mg(HCO_3)_2$ form with calcium or magnesium ions.

These complexes are initially soluble, but their accumulation brings about a continual loss of carbon dioxide ($CO_2$) which leads to an increase in the pH.

As soon as the pH is greater than or equal to approximately 7.5, the calcium and magnesium complexes are converted and precipitate in the form of virtually insoluble carbonates ($CaCO_3$ or $MgCO_3$).

To avoid these precipitations, an attempt has been made to abolish all bicarbonate ions and to retain only agents generating the said bicarbonates in vivo, such as acetate or lactate ions.

The conversion of these ions to bicarbonates is not, however, complete; in addition, there is a resultant accumulation of acetates or lactates, which contributes to an increase in the patient's acidosis, the onset of metabolic disorders and hemodynamic disorders.

Other methods have been envisaged for avoiding the formulation of insoluble carbonates:

the continuous bubbling of $CO_2$ into the dialysis solution, to maintain the pH below 7.5 and thereby avoid the formation and precipitation of calcium or magnesium carbonates;

the preparation of solutions for dialysis free from calcium and magnesium ions, and the separate and simultaneous intravenous administration of these ions;

the preparation of separate solutions, one of them, alkaline, containing the bicarbonates and the other, acidic, containing the calcium and magnesium, these two solutions being mixed at the time of dialysis;

the addition of calcium- and magnesium-complexing agents, capable of preventing their precipitation.

Not only are all these methods tedious, complicated and risky, but they also require the use of specific and costly equipment; in addition, none of these methods leads to the certain abolition of the carbonate precipitates in the apparatus of the artificial kidney or in the peritoneal cavity; finally, the application of such methods is especially thwart with problems in the case of ambulatory continuous peritoneal dialysis, which necessitates approximately 4 exchanges per 24 hours, sterile dialysates and strictly aseptic conditions.

SUMMARY OF THE INVENTION

To overcome all the drawbacks of the prior art, the present invention proposes a new stable aqueous solution of electrolytes for dialyses, based on bicarbonate ions and containing a peptide based on glycine, such as glycylglycine and also tri-, tetra, penta- and/or hexaglycines. The solution for dialyses of the present invention preferably contains 5 to 100 mmol/l of glycylglycine.

A peptide of this kind imparts great stability to the solution for dialyses, by virtue of a pH bordering on the physiological pH (7.35±0.005) endowing it with a buffering power; the pH of the solution for dialyses according to the invention is between 6.75 and 8.00, and is preferably between 7.10 and 7.60.

Apart from the peptide based on glycine, the solution of the present invention contains all the constituents customarily used for the preparation of a solution for dialyses; these constituents can be chosen, in particular, from sodium, chloride, potassium, calcium and magnesium ions and glucose and/or mixtures thereof; but other constituents may be used, such as sulfate or citrate ions. The pH and the stability of the solution of the present invention depend, as is quite obvious, on the respective amounts of its various constituents, and especially on the amount of peptide based on glycine which is incorporated.

In addition, this peptide has also proved to play the part of an osmotic agent, and the amount of it in the solution of the present invention is accordingly inversely proportional to that of an osmotic agent such as glucose.

Thus, the present invention also relates to the solutions for dialysis containing little or no glucose.

This fact represents a major advantage, in particular in the case of continuous peritoneal dialysis, where glucose has been shown to be an agent that promotes hyperglycemia in the patient, and hence arteriosclerosis.

The present invention encompasses, as is quite obvious, the use of peptides based on glycine, and in particular glycylglycine, for the preparation of compositions for dialysis.

According to the present invention, it is also possible to prepare at the time of use a solution intended more especially for hemodialysis, starting from a mixture of powders. Thus, the present invention encompasses the use of a peptide based on glycine in powder form for the preparation of such a solution at the time of use. The other constituents of the solution are, in this case, also introduced in powder form.

DETAILED DESCRIPTION OF THE INVENTION

The tables which follow show examples of solutions according to the present invention.

These solutions have an electrolyte formula similar to that of the dialysates based on lactate or acetate existing on the market.

These examples in no way limit the scope of the present invention, since all solutions for dialysis based on bicarbonates and containing glycylglycine, and especially those whose pH is between 6.75 and 7.60, form an integral part of this description.

In particular, meticulous studies undertaken in the context of the present invention have shown that the replacement of calcium chloride and magnesium chloride by calcium citrate and magnesium citrate is advantageous and clinically effective for hemodialysis. Such replacement imparts to the solutions of the present invention an increased resistance to the possible processes of crystallization of carbonates, and consequently an increased stability.

In addition, it has been shown that a slight decrease in the bicarbonate concentration (for example to 30 mmol/l) and/or a possible increase in the glycylglycine concentration contribute to improving the stability of the solutions of the present invention, and are useful, in particular, for preventing a possible alkalosis in ambulatory continuous peritoneal dialysis.

Table 1 shows three solutions (a-, b- and c-) for dialyses containing 10 mmol/l of glycylglycide ($C_4H_8N_2O_3$) and whose pH is between 7.30 and 7.40. The three solutions are distinguished by their glucose content ($C_6H_{12}O_6$). They are designated a-, b- and c-, respectively, according to whether their glucose content is 15, 25 and 42.5 g/l.

Such solutions for dialyses may be stored in plastic bags and under sterile conditions.

These solutions remain stable for more than 18 months.

Their pH does not alter and their content of calcium, magnesium and bicarbonate ions remains completely unchanged during the storage period. These solutions retain their clarity; no carbonate precipitate is observed.

Table 2 shows a solution for dialysis whose pH is between 7.0 and 7.1 and which contains 50 mmol/l of glycylglycine. This solution will be designated hereinafter by the letter d-. The osmolality of this solution is approximately 414.00.

The stability of this solution is greater than 18 months.

In vitro measurements show that such a solution for dialysis considerably increases ultrafiltration, so that a single dialysis per 24 hours (instead of four) could suffice in the case of ambulatory continuous peritoneal dialysis.

Table 3 shows a solution according to the invention containing 5 mmol/l of glycylglycine, whose pH is between 7.45 and 7.55 and which will be designated hereinafter by the letter e-.

Such a formulation is truly stable for only one month, but possesses especially potent biological efficacy in the case of circulatory disorders. Such a formulation is more especially intended for hemodialysis.

TABLE 1

| Components | g/l | $Na^+$ | $Cl^-$ | $K^+$ | $Ca^{2+}$ | $Mg^{2+}$ | $HCO_3^-$ | $C_4H_8N_2O_3$ | $C_6H_{12}O_6$ |
|---|---|---|---|---|---|---|---|---|---|
| NaCl | 5.9034 | 101.00 | 101.00 | | | | | | |
| $NaHCO_3$ | 2.9403 | 35.00 | | | | | 35.00 | | |
| KCl | 0.0745 | | 1.00 | 1.00 | | | | | |
| $C_4H_8N_2O_3$ | 1.3212 | | | | | | | 10.00 | |
| ($CaCl_2.2H_2O$) | 0.2572 | | 3.50 | | 1.75 | | | | |
| ($MgCl_2.6H_2O$) | 0.1016 | | 1.00 | | | 0.50 | | | |
| $C_6H_{12}O_6$ | a- 15.0000 | | | | | | | | 83.25 |
|  | b- 25.0000 | | | | | | | | 138.75 |
|  | c- 42.5000 | | | | | | | | 236.00 |
|  |  | 136.00 | 106.50 | 1.00 | 1.75 | 0.50 | 35.00 | 10.00 | " |
| pH: 7.35 ± 0.05 | | | | | mmol/l: a- 374.00 | | | | |
|  | | | | | b- 429.50 | | | | |
|  | | | | | c- 526.75 | | | | |

TABLE 2

| Components | g/l | $Na^+$ | $Cl^-$ | $K^+$ | $Ca^{2+}$ | $Mg^{2+}$ | $HCO_3^-$ | $C_4H_8N_2O_3$ | $C_6H_{12}O_6$ |
|---|---|---|---|---|---|---|---|---|---|
| NaCl | 5.9034 | 101.00 | 101.00 | | | | | | |
| $NaHCO_3$ | 2.9403 | 35.00 | | | | | 35.00 | | |
| KCl | 0.0745 | | 1.00 | 1.00 | | | | | |
| $C_4H_8N_2O_3$ | 6.6060 | | | | | | | 50.00 | |
| ($CaCl_2.2H_2O$) | 0.2572 | | 3.50 | | 1.75 | | | | |
| ($MgCl_2.6H_2O$) | 0.1016 | | 1.00 | | | 0.50 | | | |
| $C_6H_{12}O_6$ | 15.0000 | | | | | | | | 83.25 |
|  |  | 136.00 | 106.50 | 1.00 | 1.75 | 0.50 | 35.00 | 50.00 | 83.25 |
| PH: 7.05 ± 0.05 | | | | | mmol/l: d- 414.00 | | | | |

TABLE 3

| Substances | g/l | $Na^+$ | $Cl^-$ | $K^+$ | $Ca^{2+}$ | $Mg^{2+}$ | $HCO_3^-$ | $C_4H_8N_2O_3$ |
|---|---|---|---|---|---|---|---|---|
| NaCl | 6.0495 | 103.50 | 103.50 | | | | | |
| $NaHCO_3$ | 2.9403 | 35.00 | | | | | 35.00 | |
| KCl | 0.1118 | | 1.50 | 1.50 | | | | |
| $C_4H_8N_2O_3$ | 0.6606 | | | | | | | 5.00 |
| ($CaCl_2.2H_2O$) | 0.2572 | | 3.50 | | 1.75 | | | |
| ($MgCl_2.6H_2O$) | 0.1016 | | 1.00 | | | 0.50 | | |
|  |  | 138.50 | 109.50 | 1.50 | 1.75 | 0.50 | 35.00 | 5.00 |
| pH: 7.50 ± 0.05 | | | | | mmol/l: e- 291.75 | | | | |

The examples which follow illustrate the present invention without in any way limiting the scope thereof.

EXAMPLE 1

Preparation of the dialysates

Each solution for dialysis was prepared by diluting high grade chemical substances in very pure water produced by the method of combined reverse osmosis and demineralization (Millipore/Milli-Q). (The company Merck supplied the sodium chloride, sodium bicarbonate, potassium chloride, calcium chloride dihydrate and magnesium chloride hexahydrate. The anhydrous glucose is obtained from MALLINCKRODT. The glycylglycine or diglycine is obtained from SERVA and the company SIGMA supplied the glycylglycylglycine or triglycine).

The dialysates a-, b-, c- and d- are then filtered by means of sterile ultrafilters (PORTEX) and transferred to bottles that can be set up rapidly, equipped with airtight rubber stoppers. The bottles and stoppers are sterilized at 115° C. for 3 hours. They are stored at an ambient temperature of between 10° and 40° C.

The dialysate e- is stored without any special precaution at room temperature and exposed to the air.

EXAMPLE 2

Stability of the dialysates 2.1. Methods

With the object of assessing the stability of the dialysates, the sample is withdrawn aseptically and anaerobically by suction (the syringe is carefully placed at the surface of the solution present in the bottles). This sampling is performed at various time intervals and immediately after the preparation described in Example 1.

Biochemical studies are performed immediately. The following are measured: the pH, the amount of $HCO_3$ (Radiometer, A8L-2), the osmolality (by determination of the freezing point-Gonotec-Osmomat 030) and the amount of calcium and magnesium by absorption spectrophotometry (Perkin-Elmer 1370). Glycine and glycylglycine are assayed by a modified ninhydrin method, carried out, respectively, in hydrolyzed samples (6 moles of HCl, 24 hours at 110° C.) and unhydrolyzed samples of dialysate.

The method is specific for free glycine, giving no color for peptides based on glycine.

2.2. Results

The exceptional results obtained are recorded in the tables which follow.

Tables 4, 5 and 6 correspond, respectively, to the dialysates a-, b- and c-.

Table 7 gives the stability results for the dialysate d-.

Table 8 gives the stability results for the dialysate e-.

TABLE 4

| Months | mOsmol/kg Osmolality | pH | $HCO_3^-$ mmol/l | $Ca^+$ | $Mg^+$ | Glycyl-glycine | Glycine |
|---|---|---|---|---|---|---|---|
| 0 | 372.0 | 7.30 | 32.8 | 1.76 | 0.50 | 10.00 | nil |
| 1 | 370.0 | 7.32 | 33.0 | 1.77 | 0.51 | 9.89 | " |
| 2 | 374.0 | 7.29 | 33.0 | 1.74 | 0.52 | 10.05 | " |
| 3 | 376.5 | 7.31 | 32.4 | 1.72 | 0.50 | 9.95 | " |
| 4 | 375.0 | 7.28 | 33.2 | 1.76 | 0.48 | 10.00 | " |
| 5 | 371.5 | 7.30 | 32.5 | 1.72 | 0.54 | 10.05 | " |
| 6 | 376.0 | 7.34 | 32.0 | 1.77 | 0.50 | 10.00 | " |
| 7 | 376.6 | 7.30 | 31.8 | 1.69 | 0.50 | 9.92 | " |
| 8 | 370.0 | 7.28 | 33.0 | 1.75 | 0.51 | 10.00 | " |
| 9 | 374.0 | 7.31 | 32.2 | 1.75 | 0.49 | 9.88 | " |
| 10 | 370.0 | 7.33 | 32.4 | 1.72 | 0.48 | 10.02 | " |
| 11 | 375.0 | 7.30 | 33.0 | 1.76 | 0.52 | 9.90 | " |
| 12 | 371.5 | 7.31 | 32.0 | 1.72 | 0.50 | 9.95 | " |
| 13 | 373.0 | 7.33 | 33.5 | 1.76 | 0.50 | 9.90 | " |
| 14 | 372.0 | 7.30 | 31.5 | 1.72 | 0.53 | 10.00 | " |
| 15 | 370.0 | 7.28 | 32.5 | 1.75 | 0.51 | 10.00 | " |
| 16 | 376.0 | 7.31 | 34.0 | 1.77 | 0.50 | 10.00 | " |

TABLE 5

| Months | mOsmol/kg Osmolality | pH | $HCO_3^-$ mmol/l | $Ca^+$ | $Mg^+$ | Glycyl-glycine | Glycine |
|---|---|---|---|---|---|---|---|
| 0 | 426.0 | 7.32 | 33.5 | 1.74 | 0.51 | 10.00 | nil |
| 1 | 430.0 | 7.30 | 32.5 | 1.76 | 0.50 | 9.92 | " |
| 2 | 425.0 | 7.27 | 32.0 | 1.72 | 0.50 | 10.00 | " |
| 3 | 426.0 | 7.33 | 31.8 | 1.77 | 0.52 | 9.95 | " |
| 4 | 430.0 | 7.31 | 32.2 | 1.75 | 0.49 | 10.05 | " |
| 5 | 418.0 | 7.30 | 33.0 | 1.73 | 0.50 | 10.02 | " |
| 6 | 425.0 | 7.29 | 32.0 | 1.76 | 0.50 | 9.96 | " |
| 7 | 424.0 | 7.28 | 32.5 | 1.71 | 0.51 | 10.00 | " |
| 8 | 425.0 | 7.32 | 32.0 | 1.76 | 0.49 | 10.00 | " |
| 9 | 430.0 | 7.32 | 31.8 | 1.72 | 0.51 | 10.00 | " |
| 10 | 423.0 | 7.30 | 32.4 | 1.72 | 0.48 | 9.95 | " |
| 11 | 430.0 | 7.32 | 33.0 | 1.74 | 0.52 | 10.05 | " |
| 12 | 425.0 | 7.30 | 32.0 | 1.76 | 0.50 | 10.00 | " |
| 13 | 428.0 | 7.29 | 33.2 | 1.77 | 0.51 | 9.88 | " |
| 14 | 430.0 | 7.32 | 33.0 | 1.74 | 0.49 | 9.98 | " |
| 15 | 416.0 | 7.30 | 32.0 | 1.73 | 0.51 | 10.05 | " |

TABLE 6

| Months | mOsmol/kg Osmolality | pH | $HCO_3^-$ mmol/l | $Ca^+$ | $Mg^+$ | Glycyl-glycine | Glycine |
|---|---|---|---|---|---|---|---|
| 0 | 525.0 | 7.31 | 33.0 | 1.77 | 0.50 | 9.95 | nil |
| 1 | 528.0 | 7.30 | 32.8 | 1.75 | 0.50 | 10.05 | " |
| 2 | 531.0 | 7.28 | 32.5 | 1.72 | 0.50 | 10.00 | " |
| 3 | 520.0 | 7.28 | 32.0 | 1.77 | 0.48 | 10.00 | " |
| 4 | 423.0 | 7.28 | 32.5 | 1.75 | 0.51 | 9.98 | " |
| 5 | 531.0 | 7.29 | 32.3 | 1.76 | 0.52 | 9.95 | " |
| 6 | 514.0 | 7.30 | 31.8 | 1.74 | 0.50 | 9.95 | " |
| 7 | 517.0 | 7.31 | 32.0 | 1.75 | 0.50 | 10.05 | " |
| 8 | 530.0 | 7.30 | 32.5 | 1.72 | 0.48 | 10.00 | " |
| 9 | 523.0 | 7.28 | 32.0 | 1.74 | 0.49 | 10.00 | " |
| 10 | 521.0 | 7.30 | 32.0 | 1.72 | 0.50 | 10.05 | " |
| 11 | 532.0 | 7.31 | 32.6 | 1.76 | 0.52 | 9.90 | " |
| 12 | 531.0 | 7.29 | 32.0 | 1.74 | 0.50 | 9.92 | " |
| 13 | 516.0 | 7.31 | 31.8 | 1.75 | 0.50 | 9.98 | " |

TABLE 7

| Months | mOsmol/kg Osmolality | pH | $HCO_3^-$ mmol/l | $Ca^+$ | $Mg^+$ | Glycyl-glycine | Glycine |
|---|---|---|---|---|---|---|---|
| 0 | 415.5 | 7.10 | 32.8 | 1.74 | 0.50 | 50.5 | nil |
| 1 | 412.0 | 7.04 | 32.5 | 1.75 | 0.51 | 50.2 | " |
| 2 | 410.0 | 7.08 | 33.0 | 1.77 | 0.50 | 51.0 | " |
| 3 | 412.0 | 7.05 | 32.0 | 1.74 | 0.48 | 49.0 | " |
| 4 | 410.0 | 7.07 | 33.0 | 1.73 | 0.49 | 50.5 | " |
| 5 | 420.0 | 7.10 | 32.8 | 1.72 | 0.48 | 50.0 | " |
| 6 | 413.0 | 7.05 | 33.0 | 1.74 | 0.50 | 50.0 | " |
| 7 | 417.0 | 7.02 | 31.8 | 1.77 | 0.52 | 48.9 | " |
| 8 | 420.0 | 7.00 | 32.0 | 1.73 | 0.50 | 50.3 | " |
| 9 | 414.0 | 7.04 | 31.8 | 1.77 | 0.48 | 51.0 | " |
| 10 | 412.0 | 7.08 | 32.4 | 1.72 | 0.50 | 50.6 | " |
| 11 | 416.0 | 7.10 | 32.8 | 1.75 | 0.51 | 49.8 | " |
| 12 | 411.0 | 7.05 | 33.0 | 1.77 | 0.51 | 49.0 | " |
| 13 | 416.0 | 7.10 | 32.8 | 1.73 | 0.50 | 50.2 | " |
| 14 | 412.0 | 7.05 | 33.0 | 1.72 | 0.49 | 49.0 | " |
| 15 | 417.0 | 7.05 | 33.2 | 1.76 | 0.52 | 51.0 | " |

TABLE 7-continued

| Months | mOsmol/kg Osmolality | pH | mmol/l HCO$_3^-$ | Ca$^+$ | Mg$^+$ | Gly-cyl-gly-cine | Gly-cine |
|---|---|---|---|---|---|---|---|
| 16 | 412.0 | 7.04 | 32.5 | 1.78 | 0.50 | 51.2 | " |
| 17 | 412.0 | 7.10 | 32.0 | 1.80 | 0.50 | 49.6 | " |
| 18 | 417.0 | 7.06 | 32.8 | 1.76 | 0.51 | 49.5 | " |

TABLE 8

| Days | mOsmol/kg Osmolality | pH | mmol/l HCO$_3^-$ | Ca$^+$ | Mg$^+$ | Glycyl-glycine | Gly-cine |
|---|---|---|---|---|---|---|---|
| 0 | 290.0 | 7.48 | 33.0 | 1.75 | 0.50 | 5.00 | nil |
| 1 | 288.0 | 7.43 | 32.8 | 1.72 | 0.49 | 4.96 | " |
| 2 | 282.0 | 7.48 | 33.5 | 1.75 | 0.50 | 5.05 | " |
| 3 | 287.0 | 7.58 | 32.2 | 1.70 | 0.45 | 4.98 | " |
| 4 | 286.0 | 7.65 | 31.8 | 1.68 | 0.42 | 5.03 | " |
| 5 | 285.0 | 7.70 | 30.0 | 1.50 | 0.40 | 5.00 | " |

It has hence been shown that glycylglycine enables true buffer solutions to be produced and their stability secured.

In effect, no perceptible change in the pH, in the amounts of HCO$_3$, Ca, Mg and in the osmolality could be detected. The amount of glycylglycine remains unchanged.

Glycine is not observed in the unhydrolyzed samples of the dialysates a-, b-, c- and d- for at least one year.

The peptides based on glycine are very resistant to degradation processes. Their decomposition temperature is above 270° C.

The dialysate e- is less stable as a result of the fact that its pH, approximately equal to 7.50, is close to the critical value (between 7.55 and 7.60) which promotes the formation of insoluble calcium and magnesium carbonates.

EXAMPLE 3

Peritoneal dialysis in animals
3.1. Methods

With the object of assessing the ultrafiltration capacity of the dialysate containing bicarbonate and peptides based on glycine, a direct perfusion of 40 ml/kg of the dialysate d- (1.5% of glucose, 415 mosmol/kg) is performed into the peritoneal cavity of rabbits.

The same amount of dialysate in which the diglycine (or glycylglycine) has been replaced by an equimolar amount of triglycine is also injected, in order to carry out an additional trial (1.5% of glucose, 415 mosmol/kg).

The control dialysate used is Dianeal solution of the company Travenol (2.27% of glucose, 400 mosmol/kg).

The perfusion is carried out in 3 separate groups each containing 4 rabbits (weighing approximately 3 to 4 kg).

After a latency time of 4 hours, the rabbits are sacrificed and the peritoneal fluid carefully collected. The peritoneal membrane is studied at microscopic and histological levels.

3.2. Results

All the animals showed good toleration of the peritoneal perfusion of the dialysate based on bicarbonate and di- or tri-glycine. It is deduced from the microscopic and histological studies that no inflammation of the peritoneum has appeared.

The dialysate d- based on bicarbonate and glycylglycine has an osmolality approximately similar to that of Travenol Dianeal solution. And despite the replacement of fairly large glucose molecules of the Dianeal solution (180 daltons) by smaller diglycine molecules of the dialysate d- (132.12 daltons), the dialysate d- of the present invention permitted an ultrafiltration almost equal to that obtained with Dianeal solution, namely 7.40 versus 7.80 ml/kg for the dialysate of the invention versus Dianeal solution.

In addition, the dialysate based on bicarbonate and triglycine produces significantly more ultrafiltrate than Dianeal solution, although the two dialysates are approximately isosmotic and the sizes of the glucose and triglycine molecules are similar (180 and 189.2 daltons, respectively).

The amounts of ultrafiltrate are, in effect, 9.50 ml/kg versus 7.40 ml/kg for the dialysates of the invention and Dianeal solution, respectively.

EXAMPLE 4

Hemodialysis in man
4.1. Methods

The case is assessed of 4 patients, 2 men and 2 women from approximately 40 to 65 years of age, treated by hemodialysis with a standard acetate solution (solution y-) for 2 to 4 years and suffering for the last 4 months from substantial side effects, namely, headaches, nausea, vomiting and hypotension.

The treatment of these patients is modified using the dialysate e- of the present invention, under conditions similar to those of the previous treatment: 3 times per week for 4 hours (flowrate of the blood and the dialysate: 200 ml and 500 ml per minute, 1.0 m$^2$ cuprophane unit).

The hemodialysis is carried out using the RSP/Travenol apparatus.

The composition of the dialysates e- and y- is approximately similar as regards the calcium, sodium, potassium and magnesium concentrations. The differences between these two dialysates consist, in particular, in that the 35 mmol/l of acetate (of the dialysate y-) have been replaced by 35 mmol/l of bicarbonates and 5 mmol/l of diglycine (for the dialysate e-).

Biochemical monitoring is performed once per week: at the beginning of the dialysis, 1 hour after the initiation and immediately after the dialysis, this being carried out for 4 months for patients treated, respectively, with the dialysate y- and e-.

4.2. Results

The hemodialyzed patients showed good tolerance of the dialysate e- based on bicarbonate and glycylglycine. No side effect was noted: the incidence of headaches, vomiting, nausea and hypotension gradually decreased and then completely disappeared at the end of the first month.

The treatment by means of the dialysate e- gave better correction of the metabolic acidosis than the treatment by means of the dialysate y-. The results are recorded in Table 9 below:

TABLE 9

| | Beginning of the dialysis | 1 hour | After the dialysis |
|---|---|---|---|
| | Acetate (dialysate y-) | | |
| pH | 7.340 ± 0.045 | 7.350 ± 0.037 | 7.380 ± 0.058 |
| HCO$_3$ | 17.9 ± 2.1 | 17.0 ± 1.8 | 18.0 ± 2.6 |
| | Bicarbonate/glycylglycine (dialysate e-) | | |
| pH | 7.385 ± 0.020 | 7.420 ± 0.030 | 7.465 ± 0.030 |
| HCO$_3$ | 20.5 ± 2.0 | 24.9 ± 1.2 | 27.3 ± 1.6 |
| p< | 0.04 | 0.001 | 0.001 |

A significant increase in the pH and $HCO_3$ values was obtained during the dialysis using the dialysate e-, whereas, during the dialysis using the standard dialysate y- based on acetate, the pH slightly increased and the amount of $HCO_3$ remained virtually unchanged.

The $pCO_2$ values remained stable during the dialysis using the solution e-, whereas they decreased during the dialysis with acetate, mainly 1 hour after the initiation and at the post-dialysis check.

No difference relating to the blood concentrations of $pO_2$, Na, Cl, K, P, Ca, Mg, urea and creatine between the dialysis with the solution e- and the dialysis with acetate (y-) was noted.

The amounts of perfusion with glycylglycine are, for hemodialysis, between 24 and 32 g per dialysis (versus 100 l of dialysate) containing 5 mmol/l and, for ambulatory continuous peritoneal hemodialysis (sic), less than 7.5 g/24 hours (using 8¼ exchanges of 2 liters per day with a concentration of 10 mmol/liter).

Not only are such perfused amounts free from risk, but they can also be beneficial.

The four patients who have been treated for more than four months with the dialysate e are in excellent condition.

What is claimed:

1. A method of stabilizing an aqueous dialytic solution of electrolytes including bicarbonate ions comprising incorporating in said solution a peptide based on glycine, and selected from the group consisting of di-, tri-, tetra-, penta- and hexaglycine, said glycine being incorporated in an amount effective to substantially prevent the precipitation of carbonates.

2. A method according to claim 1 wherein said peptide based on glycine is added in powder form to said dialytic solution at the time of using said solution for dialysis.

3. A method according to any one of claims 1 or 2 wherein said peptide based on glycine is glycylglycine.

4. A method according to claim 3 wherein said solution contains glycylcine in a concentration of 5 to 100 mmol/l of solution.

5. A method according to any one of claims 1 and 2 wherein the pH of said solution is between 6.75 and 8.00.

6. A method according to any one of claims 1 and 2 wherein the pH of said solution is between 7.10 and 7.60.

7. A method according to claim 2 wherein the constituent electrolytic ions of said dialytic solution as well as the peptide based on glycine are added in powder form to said solution at the time of use.

* * * * *

UNITED STATES PATENT AND TRADEMARK OFFICE
CERTIFICATE OF CORRECTION

PATENT NO. : 4,959,175
DATED : September 25, 1990
INVENTOR(S) : Hippocrates Yatzidis It is certified that error appears in the above-identified patent and that said Letters Patent is hereby corrected as shown below:

In column 10, claim 4, line 2, delete "glycylcine" in favor of --glycylglycine--.

Signed and Sealed this

Twenty-fifth Day of February, 1992

*Attest:*

HARRY F. MANBECK, JR.

*Attesting Officer*      *Commissioner of Patents and Trademarks*